United States Patent [19]

Armstrong

[11] Patent Number: 5,475,153
[45] Date of Patent: Dec. 12, 1995

[54] PROCESS TO PRODUCE TETRABROMOBISPHENOL WITH THE REDUCED FORMATION OF ALKYL BROMIDE BY-PRODUCTS

[75] Inventor: Stuart Armstrong, Raleigh, N.C.

[73] Assignee: Great Lakes Chemical Corp., Lafayette, Ind.

[21] Appl. No.: 368,351

[22] Filed: Jan. 4, 1995

[51] Int. Cl.$^6$ .................................................. C07C 39/367
[52] U.S. Cl. ........................................... 568/726; 568/779
[58] Field of Search ...................... 568/726, 779

[56] References Cited

U.S. PATENT DOCUMENTS

| | | | |
|---|---|---|---|
| 3,029,291 | 4/1962 | Dietzler | 260/619 |
| 3,234,289 | 2/1966 | Hennis | 260/619 |
| 3,929,907 | 12/1975 | Janzon et al. | 260/619 |
| 4,180,684 | 12/1979 | Kleinschmit et al. | 568/726 |
| 4,701,568 | 10/1987 | McKinnie et al. | 568/726 |
| 5,138,103 | 8/1992 | Eguchi et al. | 568/726 |

FOREIGN PATENT DOCUMENTS

| | | | |
|---|---|---|---|
| 686772 | 5/1964 | Canada | 568/726 |
| 0472395 | 2/1992 | European Pat. Off. . | |

*Primary Examiner*—Werren B. Lone
*Attorney, Agent, or Firm*—Woodard, Emhardt, Naughton, Moriarty & McNett

[57] ABSTRACT

A process for the preparation of 4,4'-isopropylidene bis(2, 6-dibromophenol), also known as tetrabrombisphenol A, that dramatically reduces the formation of alkyl bromide by-products. Bisphenol A is brominated with a $C_3$ to $C_5$ n-alcohol in a water mixture to suppress the formation of alkyl bromides. The bisphenol A is brominated between 15° C. and 25° C. and then heated at a 55° C. to 70° C. to insure bromination is complete. The tetrabrombisphenol A is then filtered from the reaction mixture and dried. Tetrabromobisphenol A produced from this process typically has a melting point of 180° C. or higher, and is typically greater than 98% pure. Hydrogen peroxide is optionally combined with the reactants to reduce the amount of added bromine necessary for the bromination of the tetrabromobisphenol A.

11 Claims, No Drawings

PROCESS TO PRODUCE TETRABROMOBISPHENOL WITH THE REDUCED FORMATION OF ALKYL BROMIDE BY-PRODUCTS

BACKGROUND OF THE INVENTION

This invention pertains to a process of making alkylidene bis(dibromophenols) also known as tetrabromobisphenols, and more particularly to a process to produce these compounds with higher purity while simultaneously reducing the formation of alkyl bromide by-products.

Tetrabromobisphenols are readily available and widely used compounds, typically prepared by brominating bisphenols in methanol or ethanol. During preparation, the prior art processes routinely brominate the solvent as well as the biphenol. The alkyl bromides formed in the side reaction, for example methyl bromide, are separated from the tetrabromobisphenol and are presently sold. However, due to regulation by the United States government and possibly others, alkyl bromides will soon be the subject of increased environmental control and may altogether be removed from industrial production. As a result, many of the current methods to produce tetrabromobisphenols will not be commercially viable unless the alkyl bromide by-products are converted to other salable products. But given the relatively large volume of tetrabromobisphenols produced worldwide, it is unlikely that this will be an economical alternative. Therefore, another process to produce high purity tetrabromobisphenols is required, that being, one without the excessive co-formation of alkyl bromides.

U.S. Pat. No. 3,029,291 to Dietzler and U.S. Pat. No. 3,234,289 to Hennis disclose processes to form "higher purity" alkylidenebis (dibromophenols). However, "higher purity" in these early references, for example, is a product of 4,4'-isopropylidene bis(2,6-dibromophenol) with a melting point between 173° C. to 178° C. or a believed purity in excess of 95%. These melting points are likely correct, but the statements of purity are highly suspect given the advances in analytical chemistry since their publication. (Twenty-five years ago this purity data was likely derived using infra-red spectroscopy and estimates of the correlation between melting point and purity. Such a procedure is comparatively less accurate than modern analytical techniques.) Regardless, 4,4'-isopropylidene bis(2,6-dibromophenol) with melting points between 173° C. and 178° C. is commercially unacceptable today. These compounds are now needed with a purity greater than 98% or require melting points greater than 180° C. Yet, the processes disclosed in '291 and '289 only obtain this purity level upon recrystallization, and neither concerns a reduction of alkyl bromide formation which, by estimate, could be produced in these processes at a rate as high as 0.5 Kg per 1 Kg of alkylidene bis(dibromophenol) product.

SUMMARY OF THE INVENTION

In one aspect, the present invention is a process to produce tetrabromobisphenols while simultaneously reducing the formation alkyl bromide by-products. The process is preferably practiced by combining from about 2.5 to about 4 parts by mass of aqueous alcohol with 1 part by mass of alkylidenediphenol. The amount of alcohol (either propanol, butanol, or pentanol) included in the reaction mixture is preferably from about 40% to about 60% by mass of said aqueous alcohol with the balance being the total amount of water ultimately included in the reaction mixture. Although, it is not critical that all this water be introduced at the start. Some may be added later, concurrently with the bromine addition.

Next, bromine is added to the alkylidenediphenol and the aqueous alcohol to initiate the bromination reaction. It is important to substantially maintain the temperature of the reaction mixture between about 15° C. to about 25° C. with the aid of external cooling throughout this stage of the process. Typically the reaction mixture is cooled during the addition of bromine until the bromination reaction is substantially completed. It is also preferable for the bromine to be slowly added into the reaction mixture so as to assist the maintenance of the reaction temperature in this range.

After the bromination is substantially completed, the reaction mixture is then preferably heated to a temperature of from about 50° C. to about 70° C., and is maintained in this range for at least 30 minutes. This cooking step ensures that the bromination of the alkylidenediphenol is complete. Finally, the now brominated alkylidenediphenol is recovered and dried by any acceptable procedure. The product formed in the present process has a purity greater than 98% measured by liquid chromatography and is brominated without the excessive formation of alkyl bromides as compared to previously disclosed reactions.

It is an object of this invention to produce high purity tetrabromobisphenols without the excessive co-formation of alkyl bromide.

It is a feature of this invention to produce high purity tetrabromobisphenol.

It is an advantage of this invention that there is comparatively little alkyl bromide that requires disposal or conversion into other products.

DESCRIPTION OF THE PREFERRED EMBODIMENTS

Specific language is used to describe several embodiments of the present invention for the purpose of promoting an understanding of the principles of the invention. However, it must be understood that no limitation of the scope of the invention is intended by using this specific language. Any alteration and further modification of the described process and any application of the principles of the present invention are also intended that normally occur to one skilled in the art to which the present invention pertains.

Generally, the method described in the present specification is useful to prepare high-purity alkylidene bis(dibromophenols). For example; 4 4'-isopropylidene bis(2,6-dibromophenol), also known as tetrabromobisphenol A, is prepared having a purity greater than 98% as measured with liquid chromatography, or a melting point greater than 180° C. The structural formula for this example compound is shown below:

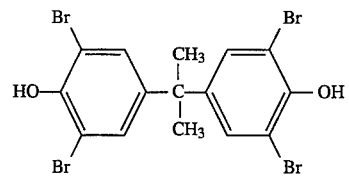

4,4'-isopropylidene bis(2,6-dibromophenol)

The present process attains this level of purity without expensive recrystallization of the product after its formation.

Furthermore, the present process is useful to reduce the undesirable formation of alkyl bromide by-products down to a level that is below that seen in the prior art. For example, levels as low as 1 g of bromopropane are formed per 1 Kg of 4,4'-isopropylidene bis(2,6-dibromophenol) product. Typical levels of 1-bromopropane formed using n-propanol as solvent and using the preferred ratios of propanol to water 1.4:1 [solvent to bisphenol A ratio 3:1], range from 5 to 10 grams per kilogram of tetrabromobisphenol A.

The process to practice this invention requires alkylidenediphenol, also known as biphenol, as a reactant. The term "alkylidenediphenol" particularly includes: 4,4'-methylenediphenol; 4,4'-ethylidenediphenol; 4,4'-isopropylidenediphenol; 4,4'-isobutylenediphenol; and 4,4'-secbutylenediphenol. These alkylidenediphenols are commercially available or readily produced by those skilled in the art of this invention. For example, 4,4'-isopropylidenediphenol may be produced from phenol and acetone, and 4,4'-secbutylenediphenol may be produced from phenol and ethyl methyl ketone. Both of these processes are described by Jenson in U.S. Pat. No. 2,468,982 and this disclosure is incorporated herein by reference. Of the alkylidenediphenols, 4,4'-isopropylidenediphenol, also known as bisphenol A, is a most preferred reactant and for convenience its structure is shown below.

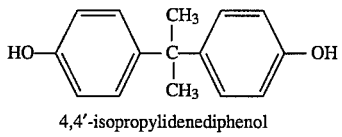

4,4'-isopropylidenediphenol

The practice of this invention first requires the alkylidenediphenol reactant to be combined with aqueous alcohol. A mixture of about 2.5 to about 4 parts by mass of aqueous alcohol is mixed with 1 part by mass of alkylidenediphenol. Suitable aqueous alcohols contain alcohol at a level of about 40% to about 60% by mass. Suitable alcohols include propanol, butanol, pentanol, or combinations of these alcohols. Preferred alcohols include n-propanol, n-butanol, and n-pentanol, with n-propanol being the most preferred. The water is usually, but not necessarily, added in at least two portions; preferably one-half with the initial alcohol charge and the other half concurrent with the last 10% to 20% of the bromine charge. The presence of water is important to convert "free" hydrogen bromide to hydrobromic acid so as to allow thorough bromination of the alkylidenediphenol, which otherwise is inhibited by the presence of HBr. The water also reduces the formation of alkyl bromides by removing HBr from the reaction.

Next, bromine is slowly added to the alkylidenediphenol mixture to form a reaction mixture and initiate the bromination of the alkylidenediphenol. As the bromination is exothermic, it is important to slowly introduce the bromine into the reaction mixture, for example, over a period of 1 to 2 hours or longer if necessary in order to maintain adequate control over reaction temperature. The temperature of the reaction mixture is preferably maintained at about 15° C. to about 25° C. with the aid of external cooling at least through the bromine addition.

A slight stoichiometric excess of bromine is preferred, typically from 4.0 to about 4.1 moles of bromine per mole of alkylidenediphenol. A decrease in hydrogen bromide concentration can facilitate bromination and reduce the amount of bromine required in the initial charge of reactants. This is achieved by the optional addition of hydrogen peroxide after bromine addition is completed. Hydrogen peroxide reacts with the hydrogen bromide to release elemental bromine, $$H_2O_2 \rightarrow 2HBr \rightarrow Br_2 + 2 H_2O$$

If hydrogen peroxide is used to practice this invention, typically the amount of bromine reactant is reduced to compensate for the additionally available bromine. Preferably, hydrogen peroxide is added in an amount to convert about 20% to about 50% of the theoretical maximum of hydrogen bromide that could form in the reaction to bromine. The use of hydrogen peroxide may also shorten the time required to brominate the alkylidenediphenol and also reduced the amount of alkylbromide formed.

Upon completion of the bromine addition and the substantial completion of the bromination of the alkylidenediphenol, the reaction mixture is then heated to about 50° C. to about 70° C. This heating or "cooking" step is preferably maintained within the reaction mixture for a time period of at least 30 minutes, but also preferably no longer than about 1 hour.

After heating is completed, the brominated alkylidenediphenol is then recovered and dried in any standard or acceptable procedure normally used to recover such a product from a reaction medium. Typically, the brominated biphenol is collected, usually by filtration, and washed with aqueous alcohol and then water, preferably hot water. Next, the wet cake is dried, perhaps in an oven or rotary evaporator. Expected crude product yields are in the range of about 96% to about 98.5%, relative to the theoretical amount of alkylidenediphenol introduced into the reaction, and crude assays vary from about 97 to 99.5% with the product having melting points 180° C. or higher.

The following Examples are provided to promote further understanding of the invention and its advantages. Thus, these examples are illustrative and not limiting in nature to the scope of the present invention described within this specification.

EXAMPLES

Example 1

130 Grams of n-propanol, 100 grams of water and 80 grams of bisphenol A were placed into a one liter reaction vessel equipped with a condenser, a stirrer, a thermometer and a dropping funnel. Thereafter, 227 grams of bromine were added over one hour at 20° C. with stirring. After the bromine was added, the temperature of the reactants was raised to 65° C. for one minute, allowed to cool to 55° C. and stirred at that temperature for 50 minutes to complete the bromination of the bisphenol A and to increase the product particle size.

The precipitated tetrabromobisphenol A was removed from the reaction mixture by filtration at 50° C. utilizing a Buchner funnel, and was subjected to washes of 20:80 n-propanol/water and then washes of hot water.

The cake was dried in a rotary evaporator at 80° C. The product thusly obtained weighed 187.4 grams, representing a 98.3% yield of the theoretical amount based on the mass of bisphenol A reactant. It was a white product which was analyzed as containing 98.5% pure tetrabromobisphenol A. Analysis (G. C.) of the mother liquor gave a total of 1.1 grams of 1-bromopropane.

Example 2

80 Grams of pentanol, 110 grams of water and 80 grams of bisphenol A were placed into a one liter reaction vessel equipped with a condenser, a stirrer, a thermometer and a dropping funnel. Thereafter, 227 grams of bromine were added over one hour at 20° C. to 25° C. with stirring. After the bromine was added, the temperature of the reactants was raised to 55 ° C. and stirred at that temperature for 2 hours to complete the bromination of the bisphenol A and to increase the product particle size.

The precipitated tetrabromobisphenol A was removed from the reaction mixture by filtration at 50° C. to 60° C. utilizing a Buchner funnel, and was subjected to two washes of 50:50 methanol/water and three 100 ml washes of hot water.

The cake was dried in a rotary evaporator at 90° C. The product thusly obtained weighed 186 grams representing a 97.6% yield of the theoretical amount based on the mass of bisphenol A reactant. It was a white product which was analyzed as containing 99.2% pure tetrabromobisphenol A.

Example 3

110 Grams of propanol, 80 grams of water and 80 grams of bisphenol A were placed into a one liter reaction vessel equipped with a condenser, a stirrer, a thermometer and a dropping funnel. Thereafter, 194 grams of bromine were added over 45 minutes at 20° C. to 25° C. with stirring. After the bromine was added, hydrogen peroxide (10.2 grams of 70% assay) was added over 15 minutes at 25° C.; the temperature was then raised to 60° C. and stirred at that temperature for 45 minutes to complete the bromination of the bisphenol A and to increase the product particle size.

The precipitated tetrabromobisphenol A was removed from the reaction mixture by filtration at 50° C. to 60° C. utilizing a Buchner funnel, and was subjected to three 30 ml washes of 20:80 propanol/water and three 100 ml washes of hot water.

The cake was dried in a rotary evaporator at 80° C. The product thusly obtained weighed 187 grams representing a 98.1% yield of the theoretical amount based on the mass of bisphenol A reactant. It was a white crystalline product which was analyzed as containing 99% pure tetrabromobisphenol A. Analysis (G.C.) of the mother liquor gave a total of 0.77 grams of 1-bromopropane.

Example 4

90 Grams of n-butanol, 100 grams of water and 80 grams of bisphenol A were placed into a one liter reaction vessel equipped with a condenser, a stirrer, a thermometer and a dropping funnel. Thereafter, 227 grams of bromine were added over 90 minutes at 20° C. to 25° C. with stirring. After the bromine addition, the temperature was raised to 60° C. and stirred at that temperature for 75 minutes to complete the bromination of the bisphenol A and to increase the product particle size.

The precipitated tetrabromobisphenol A was removed from the reaction mixture by filtration at 50° C. utilizing a Buchner funnel, and was subjected to four gram washes of hot water. The water was saturated with n-butanol.

The cake was dried in a rotary evaporator at 80° C. The product so obtained weighed 184.2 grams representing a 96.6% yield of the theoretical amount based on bisphenol A charged. It was a white product which was analyzed by liquid chromatography as containing 98.5% pure tetrabromobisphenol A. The melting point was 180.6° C.

Example 5

140 g of n-propanol, 50 g of water, and 80 g of bisphenol A were placed in a one liter reaction vessel equipped with a condenser, a stirrer, a thermometer, and a dropping funnel. Thereafter 227 grams of bromine were added over a one hour period at 20° C. After about 195 grams of bromine were placed in the reaction vessel, another 50 grams of water was slowly added concurrent with the remaining bromine addition. The temperature of the reactants was afterwards raised to 60° C. then allowed to cool to 50° C. and held at that temperature for a period of about 30 minutes. The total time from reaching 60° C. until the end of the heating cycle was one hour.

The precipitated tetrabromobisphenol A was removed from the reaction mixture by filtration utilizing a Buchner funnel and was subjected to washes of 20:30 propanol/water, followed by hot water.

The cake was dried in a rotary evaporator at 80° C. The product obtained weighed 187.4 grams representing a 98.3% yield of the theoretical amount based on the mass of bisphenol A reactant. It was a white product which was analyzed as containing 98.7% pure tetrabromobisphenol A by liquid chromatography. Analysis [G.C.] of the mother liquor gave a total of 1.40 grams of 1-bromopropane.

While the present invention is described in detail in this specification, these details are to be considered as illustrative and not restrictive in character. It should be understood that only the preferred embodiment is described and that all changes that come within the spirit of the present invention are desired to be protected.

I claim:

1. A process to produce alkylidene bis(dibromophenol), comprising the steps of:

(a) combining from about 2.5 to about 4 parts by mass of aqueous alcohol with 1 part by mass of alkylidenediphenol; wherein alcohol is from about 40% to about 60% by mass of said aqueous alcohol, and wherein said alcohol is propanol, butanol, or pentanol;

(b) adding bromine to said alkylidenediphenol and said aqueous alcohol to form a reaction mixture, while cooling said reaction mixture to a first temperature during said addition of bromine, and maintaining said first temperature in said reaction mixture until the alkylidenediphenol is substantially brominated, said first temperature ranging between about 15° C. to about 25° C.;

(c) heating said reaction mixture to a second temperature, said second temperature below the reflux temperature of said reaction mixture and also between about 50° C. to about 70° C., and maintaining said second temperature within said reaction mixture for a time period of at least about 30 minutes; and (d) recovering and drying the alkylidene bis(dibromophenol) from the reaction mixture.

2. The process of claim 1, wherein said alkylidene bis(dibromophenol) is 4,4'-isopropylidene bis(2,6-dibromophenol) and said alkylidenediphenol is 4,4'-isopropylidenediphenol.

3. The process of claim 2, wherein said 4,4'-isopropylidenediphenol has a melting point of 180° C. or higher.

4. The process of claim 2, wherein said alkylidene bis(dibromophenol) has a melting point of 181° C. to 182° C.

5. The process of claim 1, wherein said adding bromine includes a stoichiometric excess of bromine relative to said alkylidenediphenol.

6. The process of claim 1, wherein said second temperature is maintained for at least about 30 to about 60 minutes.

7. The process of claim 1, further comprising after said step (b), the additional step (e) of adding hydrogen peroxide to said reaction mixture in an amount sufficient to recover bromine from said reaction mixture.

8. The process of claim 1, wherein said alcohol is n-propanol.

9. An alkylidene bis(dibromophenol) produced by the process of claim 1.

10. 4,4'-Isopropylidene bis(2,6-dibromophenol) produced by the process of claim 1.

11. The process of claim 1, wherein about 5 to about 10 grams of n-propyl bromide is formed in a side reaction for every 1000 grams of alkylidene bis(dibromophenol) formed.

* * * * *